(12) United States Patent
Park et al.

(10) Patent No.: US 9,439,944 B2
(45) Date of Patent: *Sep. 13, 2016

(54) AGENT THAT INHIBITS ANGIOGENESIS AND METASTASIS TARGETING MTOR SIGNALING PATHWAY

(75) Inventors: Kyoungsook Park, Seoul (KR); Je-Ho Lee, Seoul (KR); Kyusam Choi, Seoul (KR)

(73) Assignee: SUNGYUNKWAN UNIVERSITY FOUNDATION FOR CORPORATE COLLABORATION, Suwon-Shi (KR)

( * ) Notice: Subject to any disclaimer, the term of this patent is extended or adjusted under 35 U.S.C. 154(b) by 970 days.

This patent is subject to a terminal disclaimer.

(21) Appl. No.: 12/107,492

(22) Filed: Apr. 22, 2008

(65) Prior Publication Data

US 2009/0264357 A1 Oct. 22, 2009

(51) Int. Cl.
- A61K 38/17 (2006.01)
- A61P 35/00 (2006.01)
- A61K 38/16 (2006.01)

(52) U.S. Cl.
CPC .................................. *A61K 38/16* (2013.01)

(58) Field of Classification Search
None
See application file for complete search history.

(56) References Cited

U.S. PATENT DOCUMENTS

2007/0021337 A1* 1/2007 Lee et al. .................... 514/12

OTHER PUBLICATIONS

Abate-Shen, C. (2002). Deregulated homeobox gene expression in cancer: cause or consequence Nature reviews 2, 777-785.
Cone, R.D., and Mulligan, R.C. (1984). High-efficiency gene transfer into mammalian cells: generation of helper-free recombinant retrovirus with broad mammalian host range. Proceedings of the National Academy of Sciences of the United States of America 81, 6349-6353.
Folkman, J. (1986). How is blood vessel growth regulated in normal and neoplastic tissue? G.H.A. Clowes memorial Award lecture. Cancer research 46, 467-473.
Folkman, J. (1989). Successful treatment of an angiogenic disease. The New England journal of medicine 320, 1211-1212.
Folkman, J. (1995). Angiogenesis in cancer, vascular, rheumatoid and other disease. Nature medicine 1, 27-31.
Folkman, J. (2007). Angiogenesis: an organizing principle for drug discovery? Nat Rev Drug Discov 6, 273-286.
Gastl, G., Hermann, T., Steurer, M., Zmija, J., Gunsilius, E., Unger, C., and Kraft, A. (1997). Angiogenesis as a target for tumor treatment. Oncology 54, 177-184.
C.J., Zuelke, C., Farkas, S., Anthuber, M., et al. (2002). Rapamycin inhibits primary and metastatic tumor growth by antiangiogenesis: involvement of vascular endothelial growth factor. Nature medicine 8, 128-135.
Hanahan, D., and Folkman, J. (1996). Patterns and emerging mechanisms of the angiogenic switch during tumorigenesis. Cell 86, 353-364.
Hartford and Rataini, M.J. (2007). Rapanycin: something old, something new, sometimes borrowed and now renewed. Clinical Pharmacology and Therapeutics. 82, 381-388.
Hwang, E.S., Kim, J., Kim, J.S., Kao, C., Ko, S.C., Chung, L., and Lee, J.H. (1998). The effects of the adenovirus-mediated wild-type p53 delivery in human epithelial ovarian cancer cell line in vitro and in vivo. Int J Gynecol Cancer 8, 27-36.
Karavanas, G., Marin, M., Salmons, B., Gunzburg, W.H., and Piechaczyk, M. (1998). Cell targeting by murine retroviral vectors. Critical reviews in oncology/hematology 28, 7-30.
Lee, S.H., Son, M.J., Oh, S.H., Rho, S.B., Park, K., Kim, Y.J., Park, M.S., and Lee, J.H. (2005). Thymosin {beta}(10) inhibits angiogenesis and tumor growth by interfering with Ras function. Cancer research 65, 137-148.
Lee, S.H., Zhang, W., Choi, J.J., Cho, Y.S., Oh, S.H., Kim, J.W., Hu, L., Xu, J., Liu, J., and Lee, J.H. (2001). Overexpression of the thymosin beta-10 gene in human ovarian cancer cells disrupts F-actin stress fiber and leads to apoptosis. Oncogene 20, 6700-6706.
Logan, J., and Shenk, T. (1984). Adenovirus tripartite leader sequence enhances translation of mRNAs late after infection. Proceedings of the National Academy of Sciences of the United States of America 81, 3655-3659.
Mackett, M., Smith, G.L., and Moss, B. (1982). Vaccinia virus: a selectable eukaryotic cloning and expression vector. Proceedings of the National Academy of Sciences of the United States of America 79, 7415-7419.
Naora, H. (2005). Developmental patterning in the wrong context: the paradox of epithelial ovarian cancers. Cell cycle (Georgetown, Tex 4, 1033-1035.
Olsson, A.K., Dimberg, A., Kreuger, J., and Claesson-Welsh, L. (2006). VEGF receptor signalling—in control of vascular function. Nat Rev Mol Cell Biol 7, 359-371.
Park, K., Kim, K., Rho, S.B., Choi, K., Kim, D., Oh, S.H., Park, J., Lee, S.H., and Lee, J.H. (2005). Homeobox Msx1 interacts with p53 tumor suppressor and inhibits tumor growth by inducing apoptosis. Cancer research 65, 749-757.
Uhr, J.W., Scheuermann, R.H., Street, N.E., and Vitetta, E.S. (1997). Cancer dormancy: opportunities for new therapeutic approaches. Nature medicine 3, 505-509.
Weidner, N., Semple, J.P., Welch, W.R., and Folkman, J. (1991). Tumor angiogenesis and metastasis—correlation in invasive breast carcinoma. The New England journal of medicine 324, 1-8.
Zhang, H., Hu, G., Wang, H., Sciavolino, P., Iler, N., Shen, M.M., and Abate-Shen, C. (1997). Heterodimerization of Msx and Dlx homeoproteins results in functional antagonism. Molecular and cellular biology 17, 2920-2932.
Landen, C.N., Jr., Birrer, M.J., and Sood, A.K. (2008). Early events in the pathogenesis of epithelial ovarian cancer. J Clin Oncol 26, 995-1005.

\* cited by examiner

*Primary Examiner* — Karen Canella
(74) *Attorney, Agent, or Firm* — Lex IP Meister, PLLC

(57) ABSTRACT

The present invention relates to a novel function of Msx1 protein for inhibiting tumor angiogenesis and metastasis by targeting mTOR (mammalian target of rapamycin) signaling pathway, and for treating a cancer in a subject. Particularly, Msx1 suppresses mTOR through a direct interaction with mTOR, resulting in the inhibition of angiogenesis. The Msx1 significantly suppresses tumor angiogenesis that is necessary for the growth, invasion, and metastasis of solid tumors. Ad-Msx1 can be used to effectively inhibit tumor metastasis by suppressing angiogenesis, tumor cell invasion, and migration.

8 Claims, 11 Drawing Sheets
(4 of 11 Drawing Sheet(s) Filed in Color)

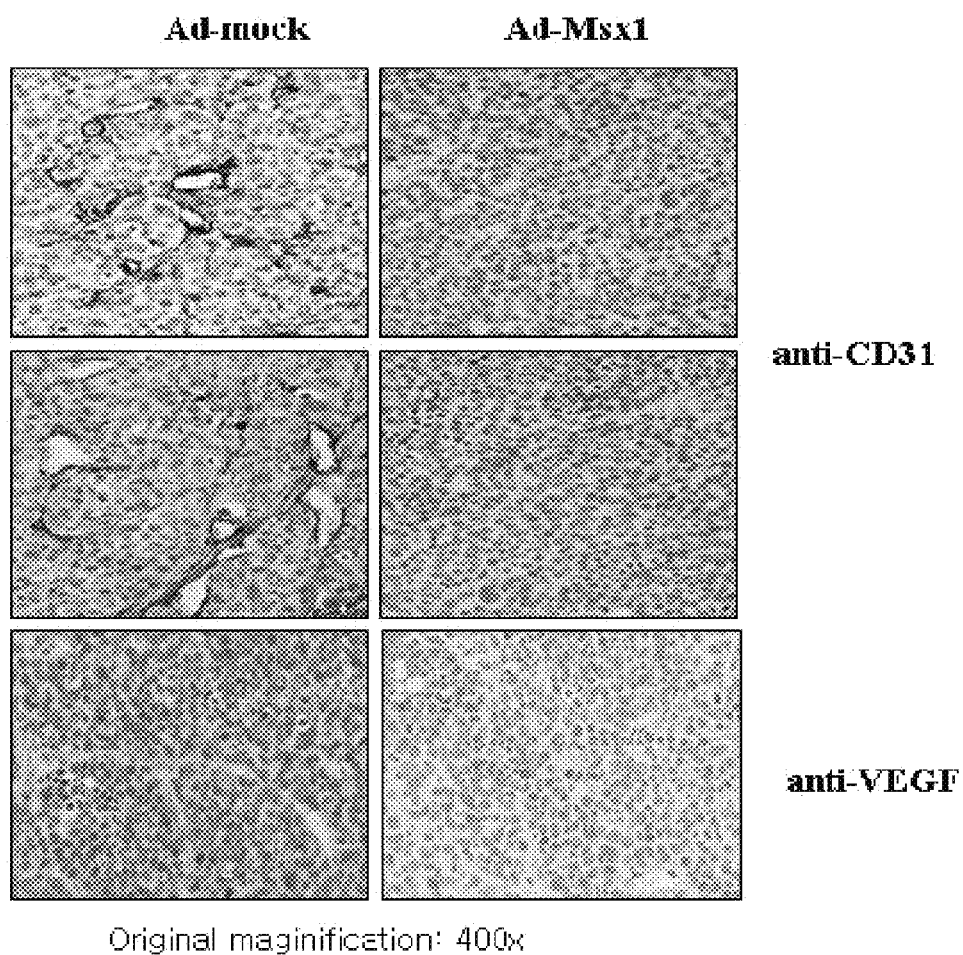

VEGF

β-Actin

SEQUENCE LISTING

```
<160> NUMBER OF SEQ ID NOS: 2

<210> SEQ ID NO 1
<211> LENGTH: 297
<212> TYPE: PRT
<213> ORGANISM: Homo sapiens

<400> SEQUENCE: 1

Met Thr Ser Leu Pro Leu Gly Val Lys Val Glu Asp Ser Ala Phe Gly
 1               5                  10                  15

Lys Pro Ala Gly Gly Ala Gly Gln Ala Pro Ser Ala Ala Ala Ala
                20                  25                  30

Thr Ala Ala Ala Met Gly Ala Asp Glu Glu Gly Ala Lys Pro Lys Val
            35                  40                  45

Ser Pro Ser Leu Leu Pro Phe Ser Val Glu Ala Leu Met Ala Asp His
        50                  55                  60

Arg Lys Pro Gly Ala Lys Glu Ser Ala Leu Ala Pro Ser Glu Gly Val
 65                  70                  75                  80

Gln Ala Ala Gly Gly Ser Ala Gln Pro Leu Gly Val Pro Pro Gly Ser
                85                  90                  95

Leu Gly Ala Pro Asp Ala Pro Ser Ser Pro Arg Pro Leu Gly His Phe
               100                 105                 110

Ser Val Gly Gly Leu Leu Lys Leu Pro Glu Asp Ala Leu Val Lys Ala
               115                 120                 125

Glu Ser Pro Glu Lys Pro Glu Arg Thr Pro Trp Met Gln Ser Pro Arg
           130                 135                 140

Phe Ser Pro Pro Pro Ala Arg Arg Leu Ser Pro Pro Ala Cys Thr Leu
145                 150                 155                 160

Arg Lys His Lys Thr Asn Arg Lys Pro Arg Thr Pro Phe Thr Thr Ala
               165                 170                 175

Gln Leu Leu Ala Leu Glu Arg Lys Phe Arg Gln Lys Gln Tyr Leu Ser
           180                 185                 190

Ile Ala Glu Arg Ala Glu Phe Ser Ser Ser Leu Ser Leu Thr Glu Thr
       195                 200                 205

Gln Val Lys Ile Trp Phe Gln Asn Arg Arg Ala Lys Ala Lys Arg Leu
   210                 215                 220

Gln Glu Ala Glu Leu Glu Lys Leu Lys Met Ala Ala Lys Pro Met Leu
225                 230                 235                 240

Pro Pro Ala Ala Phe Gly Leu Ser Phe Pro Leu Gly Gly Pro Ala Ala
                245                 250                 255

Val Ala Ala Ala Ala Gly Ala Ser Leu Tyr Gly Ala Ser Gly Pro Phe
            260                 265                 270

Gln Arg Ala Ala Leu Pro Val Ala Pro Val Gly Leu Tyr Thr Ala His
        275                 280                 285

Val Gly Tyr Ser Met Tyr His Leu Thr
    290                 295
```

```
<210> SEQ ID NO 2
<211> LENGTH: 894
<212> TYPE: DNA
<213> ORGANISM: Homo sapiens

<400> SEQUENCE: 2
atgacttctt tgccactcgg tgtcaaagtg gaggactccg ccttcggcaa gccggcgggg      60
ggaggcgcgg gccaggcccc cagcgccgcc gcggccacgg cagccgccat gggcgcggac     120 gaggagggg ccaagcccaa agtgtccct tcgctcctgc ccttcagcgt ggaggcgctc      180
atggccgacc acaggaagcc gggggccaag gagagcgccc tggcgccctc cgagggcgtg     240
caggcggcgg gtggctcggc gcagccactg ggcgtcccgc cggggtcgct gggagccccg     300
gacgcgccct cttcgccgcg gccgctcggc catttctcgg tggggggact cctcaagctg     360
ccagaagatg cgctcgtcaa agccgagagc cccgagaagc ccgagaggac cccgtggatg     420
cagagccccc gcttctcccc gccgccggcc aggcggctga gccccccagc ctgcaccctc     480
cgcaaacaca agacgaaccg taagccgcgg acgcccttca ccaccgcgca gctgctggcg     540
ctggagcgca agttccgcca gaagcagtac ctgtccatcg ccgagcgcgc ggagttctcc     600
agctcgctca gcctcactga gacgcaggtg aagatatggt tccagaaccg ccgcgccaag     660
gcaaagagac tacaagaggc agagctggag aagctgaaga tggccgccaa gcccatgctg     720
ccaccggctg ccttcggcct ctccttccct ctcggcggcc ccgcagctgt agcggccgcg     780
gcgggtgcct cgctctacgg tgcctctggc cccttccagc gcgccgcgct gcctgtggcg     840
cccgtgggac tctacacggc ccatgtgggc tacagcatgt accacctgac atag          894
```

AGENT THAT INHIBITS ANGIOGENESIS AND METASTASIS TARGETING MTOR SIGNALING PATHWAY

FIELD OF THE INVENTION

The present invention relates to methods and composition for inhibiting angiogenesis and metastasis of cancer cells using Msx1 or nucleic acids encoding the same. In addition, the present invention relate to a method and a composition for treating a cancer in a subject, comprising administering to the individual an effective amount of a therapeutically effective amount of Msx1 protein.

BACKGROUND OF THE INVENTION

Angiogenesis, the process of formation of new blood vessels, plays an important role in physiological processes such as embryonic and postnatal development as well as in wound repair. Formation of blood vessels is induced by pathological processes involving inflammation (e.g., diabetic retinopathy and arthritis) or neoplasia (e.g., cancer); (Folkman, 1995). Neovascularization is regulated by angiogenic growth factors secreted by tumor or normal cells as well as the composition of the extracellular matrix and by the activity of endothelial enzymes (Hanahan and Folkman, 1996). It has been established that growth and metastasis of solid tumors are angiogenesis-dependent (Folkman, 1986 and Folkman, 1989). A common feature of all solid tumor growth is the requirement for a blood supply. Once tumors obtain their own blood supply by inducing the growth of new capillary blood vessels, tumor cells can enter the circulation and metastasize to distant sites (Weidner, 1991). Thus, the control of angiogenesis has been an attractive target for the development of anti-cancer therapy.

Ovarian cancer is the fifth leading cause of cancer deaths among women and responsible for 4% of deaths from cancer in women (Landen et al., 2008). Despite the advances in our understanding its molecular genetics and biology, peritoneal dissemination of ovarian cancer remains a major concern for cancer-related mortality (Naora and Montell 2005). Intraperitoneal dissemination of ovarian cancer results from tumor angiogenesis and invasion. The dissemination of malignant cells from the primary tumor to local tissue or to distant organs via bloodstream or the lymphatic is a characteristic of cancer progression (Uhr, 1997 and Gastl, 1997). Angiogenesis, the formation of new blood vessels from preexisting vasculature, involves coordinated endothelial cell proliferation, migration and tube formation. This process is necessary for the growth, invasion, and metastasis of solid tumors. Angiogenesis is not only a prerequisite for tumor growth but also a major factor affecting the metastatic spread of malignant cells (Folkman, 2007). This process is influenced by growth factors, such as vascular endothelial growth factor (VEGF), and by cell adhesion molecules such as integrins. Important mediators of tumor angiogenesis are VEGF and its mitogenic receptor VEGFR-2 (Flk-1), which is localized on endothelial cells (Olsson et al., 2006). In many tumors, VEGF production is elevated and strategies to block VEGF and VEGF receptor signaling and function have resulted in significant inhibition of tumor angiogenesis and such reagents are presently in clinical trials.

Homeobox genes encode an evolutionarily conserved homeodomain and function as essential transcriptional regulators in a variety of embryonic developmental processes including cell proliferation, migration and, differentiation. Downregulation of some homeobox genes in cancer suggests them as tumor modulators (Abate-Shen, 2002). Our previous findings demonstrated that Msx1 interacts with p53 tumor suppressor and inhibits tumor growth by inducing apoptosis (Park et al., 2005).

Mammalian target of rapamycin (mTOR) is a key regulator of cell growth by controlling translation, ribosome biogenesis, autophagy, and metabolism and plays a critical role in tumorigenesis. Aberrant high activity of mTOR pathway found in many human malignancies results in not only the deregulation of cell proliferation but also tumor angiogenesis (Hartford and Rataini, 2007). Rapamycin (mTOR inhibitor) inhibits tumor growth by antiangiogenesis by inhibiting production of vascular endothelial growth factor (VEGF) (Guba et al., 2002).

The information disclosed in this background of the Invention section is only for enhancement of understanding the background of the invention and therefore, unless explicitly described to the contrary, it should not be taken as an acknowledgement or any form of suggestion that this information forms the prior art that is already known in this country to a person of ordinary skill in the art.

SUMMARY OF THE INVENTION

The present invention has been made in an effort to provide therapy that is capable of effectively modulating angiogenesis in tissues such as in tumors. The present invention relates to a novel use of Msx1 protein and nucleic acids encoding the same for inhibiting angiogenesis and for treating a cancer in a subject. Particularly, the present invention relates to compositions for modulating angiogenesis using Msx1 or nucleic acids encoding the same and use thereof in the treatment of disease states associated with angiogenesis, and this invention relates to methods and kits for inhibiting angiogenesis, tumor growth and metastasis.

The present inventors have discovered that Msx1 can effectively inhibit angiogenesis and metastasis in tumor cells.

The present invention therefore contemplates the inhibition of a tumor in a mammal by administering an effective angiogenesis-inhibiting amount of Msx1 protein or a nucleotide sequence encoding the same. In the method, the mammal is treated to produce the effect of inhibition of tube formation of vascular endothelial cells.

The present invention further contemplates a method of inhibition of angiogenesis and treatment of angiogenesis-associated diseases, including the inhibition of tumor growth, migration and metastasis.

The present invention further contemplates a method of inhibiting of angiogenesis by administering Ad-Msx1 to inhibit angiogenesis, tumor metastasis, tumor migration or tumor growth in mammals in need thereof, or to treat an angiogenesis-mediated diseases or conditions in mammals. More preferably, the Msx1 protein can be administered as a adenoviral vector or a plasmid containing an amino acid sequence comprising SEQ ID NO:1.

In one embodiment, Msx1 interacts with mTOR and inhibits mTOR-FKBP38 interaction, leading to mTOR downregulation. The consequence of mTOR downregulation results in reduction of VEGF production, which is a clear implication for antiangiogenesis.

The tumor angiogenesis is inhibited by suppressing migration and invasion of vascular endothelial cells.

In one embodiment, the present invention provides a method of treating a cancer in a subject, comprising administering to the individual an effective amount of a therapeutically effective amount of Msx1 protein consisting of an amino acid sequence of SEQ ID NO:1.

The administering comprises expressing in the tissue or the subject the Msx 1 protein. More specifically, the administering comprises introducing an adenoviral vector or plasmid including a nucleotide sequence encoding an Msx1 protein and expressing the Msx 1 protein in the tissue or the subject.

Exemplary cells or tissues include, but are not limited to, various tumors. Hence, the methods and compositions of the present invention are useful for treating disease conditions where angiogenesis is highly upregulated. Such conditions include, for example, solid tumors, including but not limited to ovarian cancers, colon cancers, cervical cancers, lung cancers, breast cancers, prostate cancers, lymphomas, and renal cell cancers.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 4A and 4B demonstrate that Ad-Msx1 inhibits vessel formation in xenograft ovarian tumor model.

DETAILED DESCRIPTION OF THE PREFERRED EMBODIMENTS

Figure 1A:
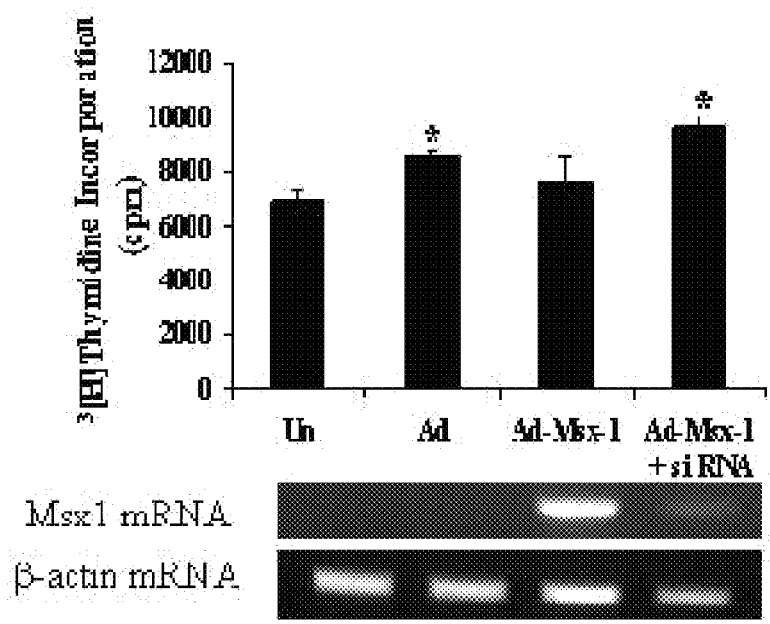
FIG. 1A to 1D illustrate that Msx1 inhibits endothelial cell migration, invasion, and tube formation in vitro.

In order that the present invention herein described may be fully understood, the following detailed description is set forth.

Unless otherwise defined, all technical terms used herein have the same meaning as commonly understood by one of ordinary skill in the pertinent art. Commonly understood definitions of molecular biology terms can be found in, for example, Rieger et al., Glossary of Genetics: Classical and Molecular, 5th edition, Springer-Verlag: New York, 1991; and Lewin, Genes VIII, Oxford University Press: New York, 2004.

The present inventors explored the role of Msx1 on angiogenesis. Overexpression of Msx1 in human umbilical vascular endothelial cells (HUVECs) inhibits angiogenesis by suppressing tube formation, migration, and invasion as well as inhibits vessel sprouting ex vivo and vessel formation in vivo. Moreover, silencing of Msx1 by siRNA abrogates its anti-angiogenic effects. Ad-Msx1 injection into a xenograft model of human ovarian cancer markedly inhibits tumor growth and tumor vascularity. Overexpression of Msx1 inhibits tumor cell invasion in vitro and also suppressed VEGF production. Consistent with its anti-angiogenic function, Ad-Msx1 injection into a xenograft intraperitoneal model of human 2774 ovarian cancer markedly inhibited tumor vascularity and suppressed experimental lung metastasis. Our findings provide evidence of the anti-angiogenic function of Msx1 in vivo and in vitro and suggest a possibility of Msx1 in anti-angiogenic cancer therapy.

The present invention is based on the discovery of a novel use of Msx1 for inhibiting angiogenesis. Gene/nucleic acid expression vectors for expressing Msx1 or any functionally equivalent variant thereof, can be prepared by methods that are well-known in the art.

Further, Msx1 or a gene encoding the same may be selected from known sequences of human or mouse.

As used herein, the term "gene" is well-known in the art and refers to a nucleic acid sequence defining a single protein or polypeptide. It will be readily recognized by those of ordinary skill that the nucleic acid sequence of the present invention can be incorporated into any one of numerous kits which are well-known in the art.

Also encompassed by the present invention is a mutant at the nucleic acid level that does not change an amino acid such as a degenerate variant due to the degeneracy of the genetic code.

A nucleic acid sequence encoding Msx1 protein for the present invention encompasses genomic DNA, cDNA, and synthetic or recombinantly produced DNA, all of which can be prepared by methods that are well-known in the art. For example, genomic DNA is extracted from cells expressing Msx1 protein, which is subsequently used for the construction of a genomic library using vectors such as plasmid, phage, cosmid, BAC, and PAC followed by colony hybridization or plaque hybridization depending on the vectors to screen the Mxs1 genomic DNA using a probe with a sequence specific for the Msx1 gene of the present invention. For the preparation of cDNA, mRNA extracted from cells expressing Msx1 protein is used to synthesize first strand cDNA by reverse-transcription followed by PCR for the amplification of cDNA encoding Msx1 protein thereof using primers specific for Msx1 of the present invention.

For example, for the purpose of the present invention, an Msx1 protein sequence with, but not limited to, NCBI (National Center for Biotechnology Information) accession no. AAH21285 or a gene encoding the same with, but not limited to, GenBank accession no. BC021285 may be used.

As mentioned hereinabove, Msx1 protein or a nucleotide sequence encoding the same of the present invention can effectively inhibit angiogenesis in a cell.

The Msx1 or a nucleotide sequence encoding the same, and a pharmaceutical composition containing the same can therefore be used effectively to treat cells or tissues associated with the disease condition. In another embodiment, a disease condition includes, but is not limited to, solid tumors such as ovarian cancers, colon cancers, cervical cancers, lung cancers, lymphomas, breast cancers, prostate cancers and renal cell cancers. The present invention further contemplates a method of inhibition of angiogenesis and treatment of angiogenesis-associated diseases, including the inhibition of tumor growth, migration and metastasis.

For the expression of Msx1 for the methods and compositions of the present invention, Msx1 gene or functional variant thereof as described herein is operatively linked into a vector. The choice of said vector depends, as is well-known in the art, on the desired level of protein expression, the host cell to be transfected, and the like. A vector contemplated by the present invention is at least capable of directing the replication and expression of a gene included in the vector in cells, preferably in eukaryotic cells.

Such eukaryotic expression vectors encompass both viral and non-viral vectors, and are familiar to one of ordinary skill in the pertinent art. For non-viral vector systems, see examples of Ausebel, et al., in Current Protocols in Molecular Biology, Wiley and Sons, New York (1993) and of Sambrook et al, Molecular Cloning: A Laboratory Manual, Cold Spring Harbor Laboratory (1989). In addition, they are commercially available from several sources. Typical of such vectors are pCDNA 3 or 4, pRc/CMV (Invitrogen, Carlsbad, Calif., USA), pSVL, and pKSV-10 (Amersham Pharmacia Biotech, Piscataway, N.J., USA).

The viral expression vectors for the expression of Msx1 thereof include infectious vectors such as recombinant DNA viruses and adenoviral or retroviral vectors which are engineered to express the desired protein and have features that allow infection of target tissues, for example, such viral vectors are used encapsulated by a viral coat, which is familiar to one of ordinary skill in the pertinent art (see Logan et al., 1984; Mackett et al., 1982; Cone et al., 1984). Further, retroviral/adenoviral expression systems can be readily adapted for practice of the methods and compositions of the present invention. For example, see Karavanas et al. (1998) for retroviral viral vectors, and Gene Expression Systems ed., Fernandez and Hoeffler, Academic Press, San Diego, USA (1990) for adenoviral expression systems. In one embodiment, Msx1 is expressed using adenoviral expression systems such as described in Park et al. (2005).

In one aspect, the present invention provides a method of pharmaceutical composition comprising an amount effective of Msx1 protein or a nucleotide sequence encoding the same to inhibit angiogenesis, tumor metastasis, tumor migration or tumor growth in a mammal in need thereof, or to treat an angiogenesis-mediated diseases or conditions in mammals. More preferably, the Msx1 protein can be administered as a vector or a plasmid a nucleotide sequence encoding a Msx1 protein having an amino acid sequence comprising SEQ ID NO:1. As used herein, the term "therapeutically effective" amount refers to an amount of Msx1 or a nucleotide sequence encoding the same that is sufficient to produce a measurable modulation, preferably inhibition, of angiogenesis in tissue or a subject. The subject is a patient to be treated, wherein the patient is a human as well as a veterinary patient.

The pharmaceutical composition containing Msx1 thereof or a nucleotide sequence encoding the same of the present invention is administered in a manner compatible with the dosage formulation, and in a therapeutically effective amount, for example intravenously, intraperitoneally, intramuscularly, subcutaneously, and intradermally. It may also be administered by any of the other numerous techniques known to those of skill in the art, see for example the latest edition of Remington's Pharmaceutical Science, the entire teachings of which are incorporated herein by reference.

For example, for injections, Msx1 or a nucleotide sequence encoding the same of the present invention may be formulated in adequate solutions including but not limited to physiologically compatible buffers such as Hank's solution, Ringer's solution, or a physiological saline buffer. The solutions may contain formulatory agents such as suspending, stabilizing, and/or dispersing agents. Alternatively, Msx1 thereof or a nucleotide sequence encoding the same of the present invention may be in powder form for combination with a suitable vehicle, e.g., sterile pyrogen-free water, before use.

Further, the composition of the present invention may be administered per se or may be applied as an appropriate formulation together with pharmaceutically acceptable carriers, diluents, or excipients that are well-known in the art.

In addition, other pharmaceutical delivery systems such as liposomes and emulsions that are well-known in the art, and a sustained-release system, such as semi-permeable matrices of solid polymers containing the therapeutic agent, may be employed. Various sustained-release materials have been established and are well-known to one skilled in the art.

Further, the composition of the present invention can be administered alone or together with another therapy conventionally used for the treatment of angiogenesis, tumor progression, and/or metastasis related diseases, such as surgical operation, hormone therapy, chemotherapy, or biological agents.

The quantity to be administered and timing may vary within a range depending on the formulation, the route of administration, and the tissue or subject to be treated, e.g., the patient's age, body weight, overall health, and other factors. For the nucleic acid sequence, the amount administered depends on the properties of the expression vector, the tissue to be treated, and the like. The suitable amount can be measured by the amount of vector used, or the amount of expressed protein expected. The exact formulation, route of administration, and dose can be chosen by the individual physician in view of the patient's condition (see, for dose and dosing schedule, e.g., latest editions of Remington's Pharmaceutical Science, Mark Publishing Co., Easton, Pa.; and Goodman and Gilman's: The Pharmacological Basis of Therapeutics, Pergamon Press).

The dosage of Msx1 thereof or a nucleotide sequence encoding the same of the present invention preferably falls within a range of concentrations that include the effective dose with little or no toxicity, but that are sufficient to produce a measurable modulation, preferably inhibition, of angiogenesis, tumor progression, and metastasis in tissue or a subject. A single dose of Msx1 thereof or a nucleotide sequence encoding the same administered will typically be in the range of about 0.05 to about 10 mg/kg of patient weight. The Msx1 thereof or a nucleotide sequence encoding the same of the present invention will typically be formulated in a suitable formulation at concentrations of about 0.001 mg/ml to 100 mg/ml such that the final dose is about 0.05 to 10 mg/kg of patient body weight. For viral vectors, the recombinant virus containing such viral vectors will typically be in the range of about $10^8 \sim 10^{12}$ pfu/kg per kg of body weight.

The following examples illustrate the present invention in further detail. However, it is understood that the present invention is not limited by these examples.

EXAMPLE 1

Construction of Various Expression Vectors

Various viral and non-viral vectors containing Msx1 full-length were constructed and used to investigate the anti-angiogenic activity of Msx1 of the present invention as previously described (Park et al., Cancer Res. 65: 749-757, 2005; Hwang et al., Int. J. Gynecol. Cancer 8: 27-36, 1998).

Adenoviral Vectors

The adenovirus vector expressing Msx1 (Ad-Msx1) was constructed according to the protocol described previously (Park et al., 2005). Briefly, a high-fidelity polymerase chain reaction (PCR)-amplified full-length mouse Msx1 cDNA fragment was cloned into HindIII/Xho I site of the adenoviral plasmid shuttle vector, pΔACMVp(A) vector. The sequence of the cloned mouse Msx1 cDNA was confirmed by DNA sequence analysis. The resulting adenoviral vector was transfected into human embryonic kidney 293 cells for adenovirus production, as previously described (Park et al., 2003). Large batches of recombinant adenovirus were purified by centrifugation through two consecutive cesium chloride gradients. Adenovirus containing an empty shuttle vector was used as a control. For the production of replication deficient adenoviruses, adenoviral constructs as described above and pJM17 carrying adenoviral genomic DNA (F. Graham, McMaster University, Ontario, Canada) were cotransfected to HEK 293 cells and purified by CsCl gradient centrifugation followed by extensive dialysis against PBS (Phosphate Buffered Saline) supplemented with 10% glycerol and Immol/L $MgCl_2$. The titer of each adenovirus produced was determined by plaque assay using HEK 293 cells and expressed as pfu (Plaque Forming Unit).

Plasmid Vectors

Plasmid vectors, pCB6/Msx1 encoding full length human Msx1 were previously described (Zhang et al., Mol. Cell Biol. 17: 2920-2932, 1997). Flag-Msx1 encoding full length human Msx1 tagged with Flag peptide was prepared by subcloning the PCR amplified a full-length Msx1 DNA into EcoR1-Xho I-digested Flag-vector. The correctness of the cloned sequence of each plasmid constructed and used for the present invention was confirmed by DNA sequencing of the constructs. siRNA (small interfering RNA) was used to knock down the expression of Msx1. The siRNA targeting Msx1 corresponding to nucleotides 199 to 217 in the human Msx1 sequence was synthesized in Dharmacon (Chicago, Ill.) and transfected into cells according to the manufacturer's instructions (Qiagen). Cultured mammalian cells were infected with Ad-Msx1 alone or Ad-Msx1 with siRNA (100 nM). The residue numbers provided are from human Msx1 sequence of NCBI accession no. AAH21285.

EXAMPLE 2

Cell Culture and Transfection

HUVEC (human umbilical vein endothelial cell, Clontech, San Diego, Calif., USA), human ovarian cancer cell line 2774 (Clontech Laboratories, Palo Alto, Calif.), Cervical cancer cell line HeLa ((American Type Culture Collection, USA), Human lung cancer cell line H1299 (American Type Culture Collection, USA), and HEK 293 (Clontech Laboratories, San Diego, Calif., USA) were maintained according to ATCC instructions and as described (Park et al, ibid). Briefly, 277, HeLa, H1299, and HEK 293 cells were cultured in DMEM (Dulbecco's Modification of Eagles Medium) and EMEM (Eagles Minimum Essential Medium), respectively, each supplemented with 10% FBS and antibiotics (Life Technologies, Gaithersburg, Md., USA). HUVECs were grown on a plate coated with 0.3% gelatin using an EGM-2 kit (Clontech Laboratories). The cells were incubated at 37° C. in a 5% $CO_2$/95% air atmosphere. DNA transfection into each of the above cell lines and adenoviral infection were carried out as described (Lee et al., Oncogene (2001) 20:6700-6776; Lee et al., Cancer Res (2005) 65, 137, Park et al., ibid).

EXAMPLE 3

Msx1 Inhibit the Endothelial Cell Migration, Invasion, and Tube Formation in Vitro To investigate the effect of Msx1 on endothelial cell migration, invasion, and tube formation in vitro, HUVEC cells were infected with adenovirus containing an empty vector or adenovirus expressing Msx1 (Ad-Msx1), followed by transfection with siRNA targeting Msx1. For the migration assay, transwell migration assay was carried out (8 μm pore size, Costar, Cambirge, Mass.) as described (Lee et al., Cancer Res, 2005, 65, 137). The lower surface of a filter was coated with 10 μg of gelatin. Lower wells were filled with M199 (Life Technologies) containing 1% FBS with VEGF (25 ng/ml). After 18 hours after the infection, cells were treated with 10 ng/ml of VEGF (R&D systems, Minneapolis, Minn., USA) for 24 hours and then cells were fixed and stained with H&E (hematoxylin and Eosin, BioRad, Hercules, Calif., USA). Non-migrating cells remaining on the upper surface of the filter were removed by wiping the cells with a cotton swab. The number of cells that migrated into the lower side of the filter were counted under a light microscope, and the mean values of eight fields were calculated. The siRNA oligonucleotide sequence targeting Msx1 corresponded to nucleotides 199-217 in the human Msx1 sequence was synthesized in Dharmacon and then 100 nM of Msx1 siRNA was used to knockdown the expression of Msx1 using an Oligofectamin reagent (Invitrogen, San Diego, Calif.) according to the manufacturer's instructions.

For the invasion assay, the lower and upper surfaces of a filter were coated with 10 μg of gelatin and 10 μg of Matrigel (BD Biosciences, Bedford, Mass.), respectively. Upper wells were plated with uninfected HUVECs and HUVECs transfected with Ad, Ad-Msx1, and Ad-Msx1+siRNAMsx1 and then incubated for 30 hours. The cells were then fixed and stained, and then quantitated as above. Migration and invasion were significantly reduced by the treatment of cells with Ad-Msx1. In contrast, knockdown of Msx1 by siRNA abrogated the migration and invasion, clearly demonstrating that such inhibitory effects of endothelial cell migration and invasion are indeed attributed to Msx1. Also Msx1 inhibits tube formation and such inhibitory effect of Msx1 on tube formation was abrogated after siRNA Msx1 transfection. These results clearly demonstrate that Msx1 of the present invention can be used to effectively inhibit tube formation that is important for angiogenesis.

FIG. 1A, HUVECs were either uninfected (Un) or infected with Ad, Ad-Msx1, or Ad-Msx1 with Msx1 small interfering RNA (Ad-Msx1+Msx1 siRNA) for 18 h and then treated with VEGF (10 ng/ml) for 24 h. Incorporated 3[H]-thymidine was determined by a liquid scintillation counting. Small interfering RNA (siRNA)-mediated suppression of Msx1 in HUVECs.

Figure 1B:
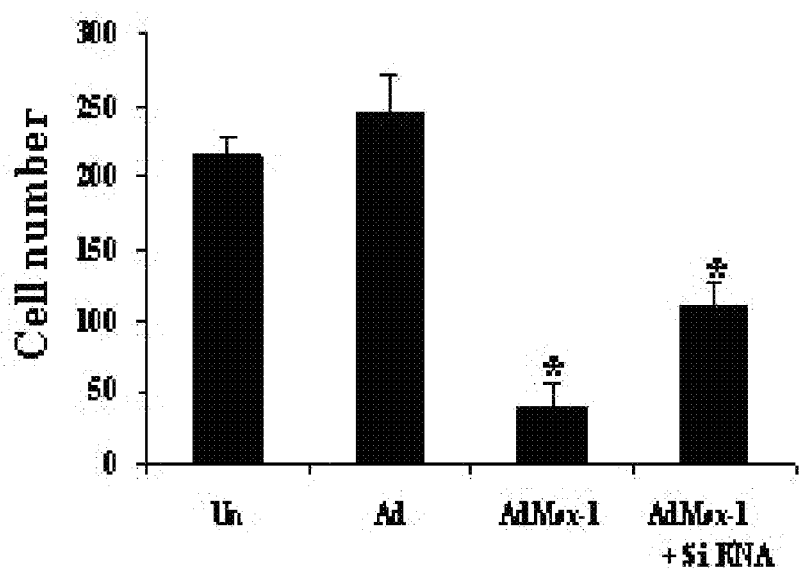
Figure 1C:
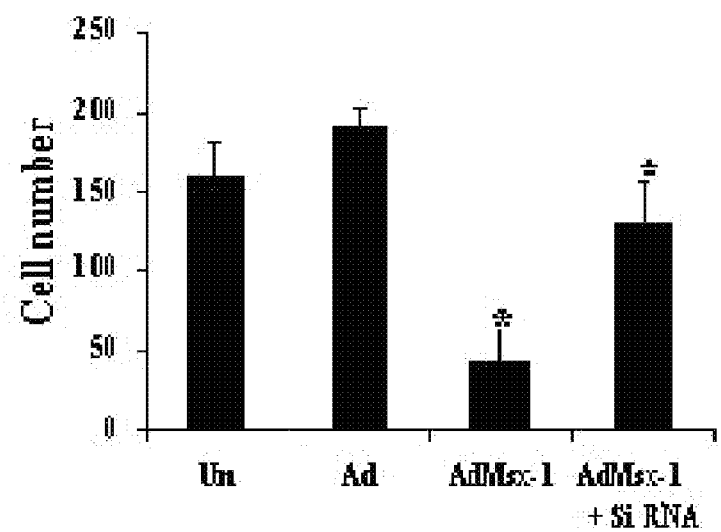

FIGS. 1B and 1C, Uninfected HUVECs and indicated adenovirus-infected HUVECs were seeded onto Transwells for migration assay (B) or on Matrigel-coated Transwells for invasion assay (C), followed by stimulation with VEGF (25 ng/ml) for 24 h or 30 h, respectively. The number of migrated or invaded cells was counted under a light microscope and mean values were determined. Independent experiments were repeated three times and error bars correspond to 95% confidence intervals. *P<0.05 compared to uninfected cells without VEGF.

Figure 1D:
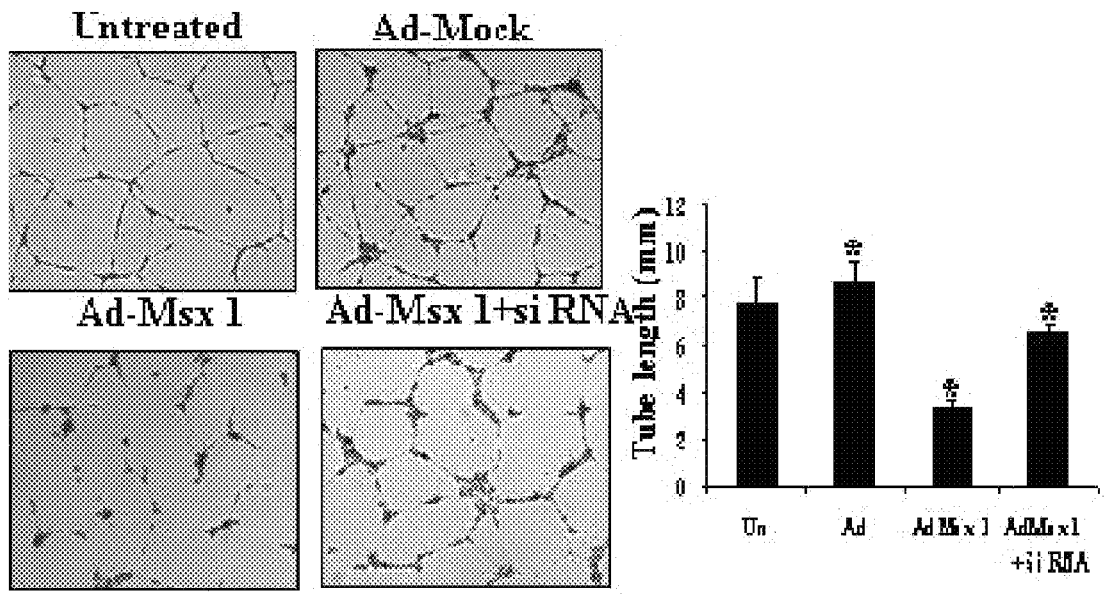

FIG. 1D, Uninfected HUVECs and adenovirus-infected HUVECs were plated on growth factor-reduced Matrigel and then treated with or without VEGF (10 ng/ml) for 48 h. The formation of tubular structure was detected by an inverted microscope. Scale bar: 100 micro meters. Tube lengths were quantified and error bars correspond to 95% confidence intervals. *P<0.05 compared to uninfected control.

EXAMPLE 4

Ad-Msx1 Suppresses VEGF Promoter Activity

The human VEGF promoter luciferase reporter constructs were described previously (JBC 2002). HUVEC cells at 70% confluency were transiently transfected with VEGF reporter construct and Ad-Msx1. As an internal control to correct for variations in transfection efficiency, 20 ng of pRL-TK (Promega, Madison, Wis.), was cotransfected. The transfections were performed using Effectene transfection reagent (Qiagen) according to the manufacturer's instructions. Luciferase activity was measured using a dual luciferase reporter assay system (Promega) according to the manufacturer's instructions, and this was normalized for the Renilla luciferase activity to correct for variations in the transfection efficiency.

Figure 2:
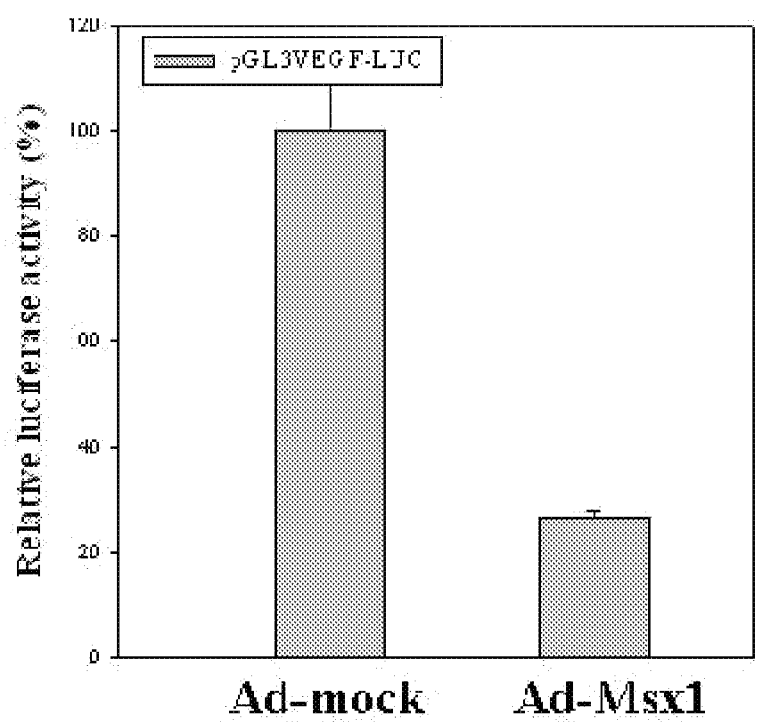
FIG. 2 shows that Msx1 suppress VEGF promoter activity.

In FIG. 2, HUVEC cells were transfected with pGL3VEGF-Luc reporter and then infected with Ad-mock or Ad-Msx1 for 24 h. Luciferase activity was determined using the luciferase assay system according to the manufacturer's protocol (Promega). Activities shown here correspond to luciferase expression relative to that of Ad-mock treated luciferase.

EXAMPLE 5

Msx1 Inhibits Vessel Sprouting Ex Vivo and In Vivo Angiogenesis

The inhibitory effect of Msx1 on ex vivo angiogenesis was investigated using an ex vivo explant culture of skeletal muscle on Matrigel as described (Jang et al., Molecular Therapy, 2004, 9, 464). Briefly, 6 week-old Balb/c mice were anesthetized, and the legs were shaved and then electrophoresed with a plasmid vector alone or Msx1-expressing plasmid. The tibialis anterior muscle was removed and washed with PBS (phosphate buffered saline) three times. The muscle was then placed in a 24-well plate containing Matrigel, followed by polymerization at 37° C. for 30 minutes. An M199 medium containing 1% FBS with or without 10 ng/ml of VEGF was added and the plates were incubated. After 6 days, outgrowth of capillary-like structures was observed and then the mean area of vascular sprouting was quantified by an optical imaging technique and ImageLab imaging software.

Figure 3A:
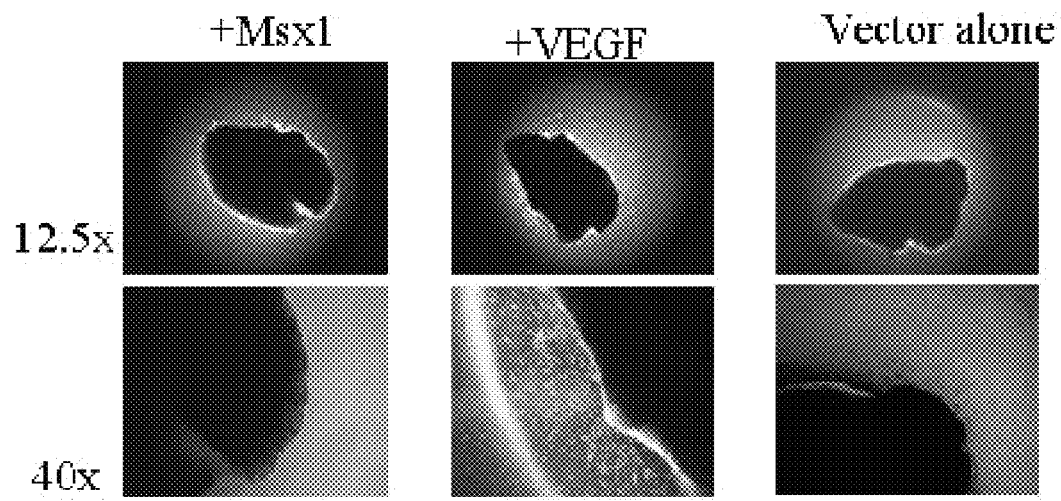
FIGS. 3A and 3B demonstrate that Msx1 inhibits vessel sprouting ex vivo and angiogenesis in vivo.

In FIG. 3A, cross-sections of mouse tibialis anterior muscle were embedded in growth factor-reduced Matrigel with or without VEGF and then treated with vector alone or Msx1 expression plasmid. Outgrowth of capillary-like structures was observed with an inverted microscope. (Original magnifications: ×12.5 (upper); ×40 (lower). The mean area of vascular sprouting was quantified and error bars correspond to 95% confidence intervals. *P<0.005 compared to uninfected control with VEGF. Similar inhibitory effects on tube formation and vessel sprouting by Msx1 overexpression were observed in three independent experiments, respectively.

Figure 3B:
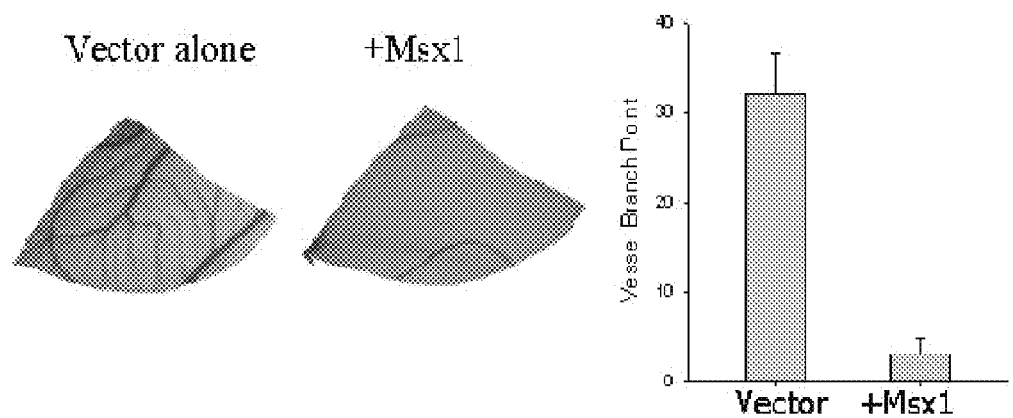

In FIG. 3B, Ad-Msx1 inhibits angiogenesis in vivo. Ten day-old CAMs (chorionic amniotic membrane) were treated with either DMSO or recombinant Msx1 dissolved in DMSO. After 72 h, CAMs were harvested and vascular density was assessed by microscopy. Angiogenesis was quantitated by counting the number of branch points arising from the vessels in a given area. Measurements were made in 6 samples infected with DMSO or recombinant Msx1 from two separate experiments. Statistical significance was assessed using a paired t test.

EXAMPLE 6

Msx1 Inhibits Angiogenesis In Vivo

Specific pathogen-free BALB/c and nu/nu mice were supplied by Charles River Lab (Japan). All animal studies were reviewed and approved by the Institutional Animal Care and Use Committee (IACUC) of Samsung Biomedical Research Institute (SBRI). SBRI is an Association for Assessment and Accreditation of Laboratory Animal Care International (AAALAC International) accredited facility and abide by the Institute of Laboratory Animal resources (ILAR) guide. Female BALB/c nude (nu/nu) mice (5 weeks old) were purchased from Charles River Laboratory (Japan), and housed under pathogen-free conditions. The Animal are and Uses Committee of Samsung Biomedical Research Institute approved the animal experiments described herein. Each experiment group included 10 animals. To establish tumors in mice, $1 \times 10^6$ 2774 tumor cells were injected intraperitoneally. Tumors were allowed to grow for 7 days. An intraperitoneal injection of $5 \times 10^8$ pfu/40 µl of Ad-Msx1 was performed twice at 4 day interval. GFP expressing tumors were examined using Illumatool tunable lighting system (Lightools Research). Mice were sacrificed on day 20 after virus injection. Tumors were then excised and prepared for immunohistochemistry. Frozen sections were processed for immunohistochemistry with indicated rat monoclonal anti-mouse CD31 (PECAM-1) antibody (PharMingen) and anti-VEGF antibody (Santa Cruz). The specificity of the staining was confirmed with isotype-matched antibodies.

In FIG. 4A, Human 2774 ovarian cancer cells were injected intraperitoneally. After 14 days, an intraperitoneal injection of Ad-mock (□) and Ad-Msx1 (●) was performed four times at $5 \times 10^8$. Frozen sections of the tumors from Ad-mock and Ad-Msx1 treated mice were stained for endothelial cells using anti-CD31 (PECAM-1) or anti-VEGF antibody.

Figure 4B:
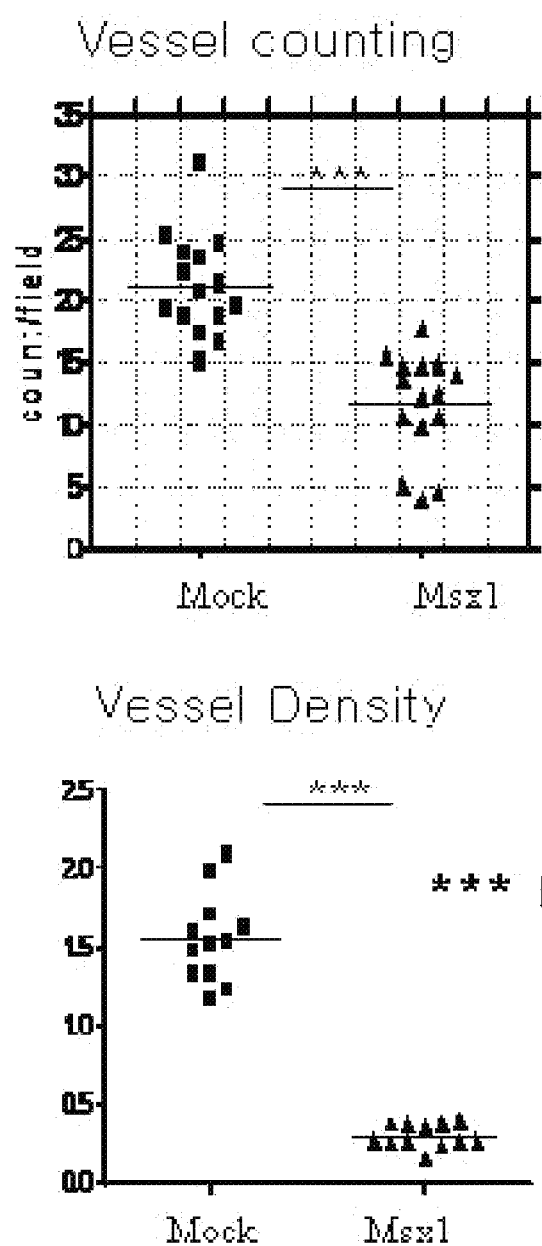

In FIG. 4B, Both vessel numbers and vascular density in tumor sections were calculated by counting the number of blood vessels and vessel density in 12-15 separate tumor cross-sections per group. ***P<0.001 compared to Ad-mock.

EXAMPLE 7

Msx1 Inhibits Spontaneous Lung Metastasis

For the experimental metastatic assays, B16F10 melanoma cells ($4 \times 10^5$ cells) mixed with $2 \times 10^3$ pfu of Ad-mock or Ad-Msx1 were injected into the tail vain of C57BL mice. After 3 weeks, the mice were sacrificed and then their lungs were removed for counting the numbers of lung melanoma metastatic colonies. The lung tissues were lysed as described previously (Lee et al. 2002). Total proteins were immunoblotted with specific antibodies to VEGF, pERK, NF-kB (all obtained from Santa cruz), as well as β-actin antibody (Sigma) as a loading control. The results were analyzed by the Mann-Whitney U test for statistical significances. Differences were considered significant at P values <0.05 (two-tailed).

Figure 5A:
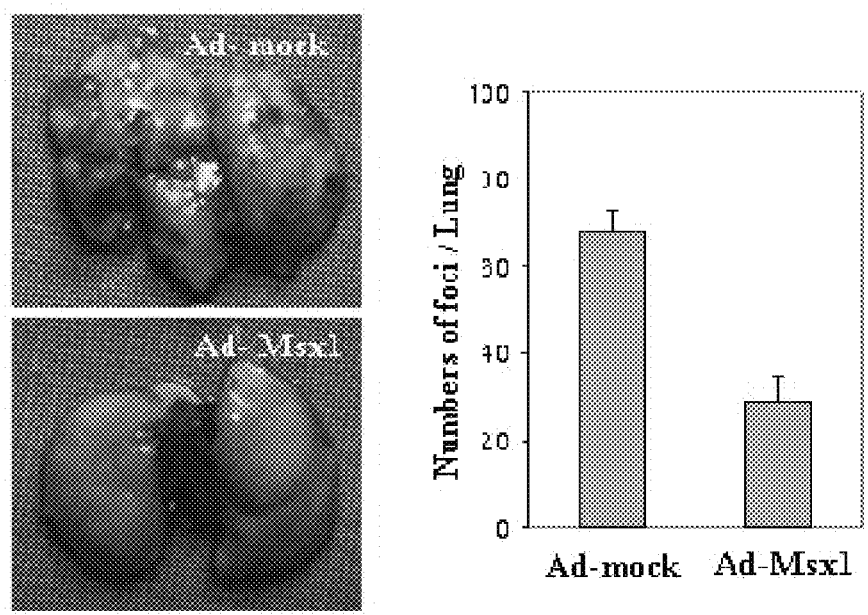
FIGS. 5A and 5B show that Msx1 inhibits spontaneous lung metastasis.

In FIG. 5A, Ad-Msx1 decreases spontaneous lung metastasis. B16F10 melanoma cells were mixed with Ad-Msx1 or Ad-mock and then injected into the tail vein. Numbers of foci by growth of B16F10 melanoma cells on the lung were counted and then plotted. *P<0.05 compared to Ad-mock.

Figure 5B:
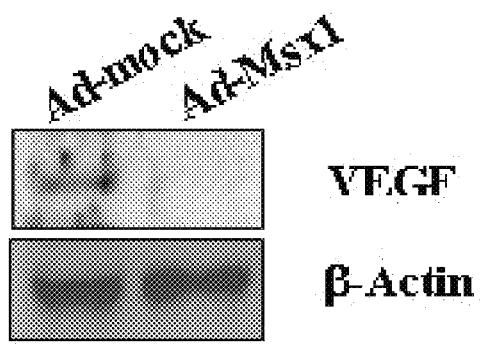

In FIG. 5B, Ad-Msx1 treatment reduced the expression of VEGF significantly. Whole tissue lysates from Ad-Msx1 or Ad-mock treated tumor tissues were prepared and then expression of VEGF protein was determined by immunoblotting with anti-VEGF antibody.

EXAMPLE 8

Msx1 Interacts with mTOR and Suppresses mTOR Signaling

Figure 6A:
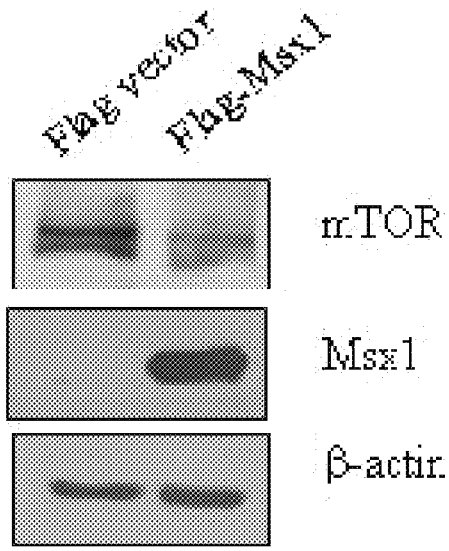
FIGS. 6A and 6B show that Msx1 downregulates mTOR and mTOR targets
Figure 6B:
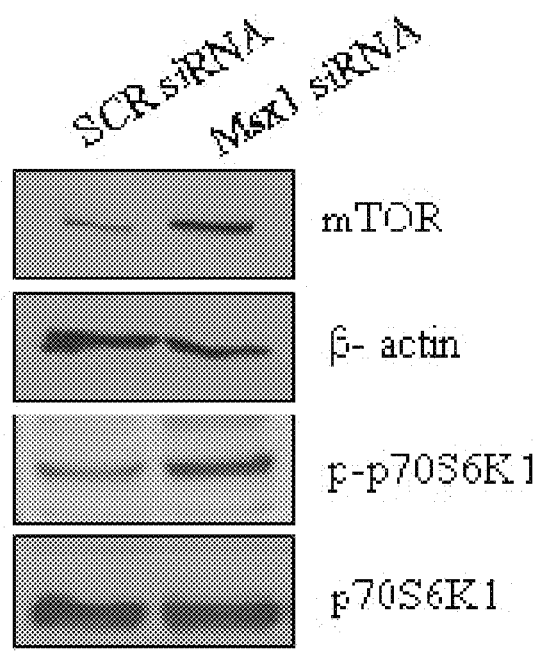

In FIG. 6A, Msx1 suppresses mTOR expression and activity. A. HEK 293 cells were transiently transfected with Flag-tagged control vector (Flag-vector) or Flag-tagged full-length Msx1 expression construct (Flag-Msx1) and then whole cell lysates were subjected to immunoblotting analysis with indicated antibody. B. Knockdown of endogenous Msx1 expression failed to inhibit mTOR downregulation and mTOR target, p70S6K1. Scrambled or Msx1—specific siRNA was transfected into HEK 293 cells using Oligofectamin and then whole cell extract was immunoblotted with indicated antibody.

Figure 7A:
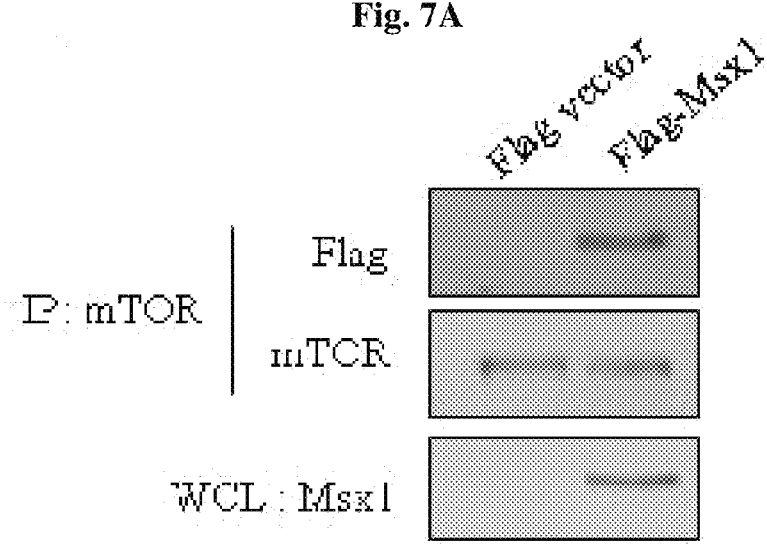
FIGS. 7A to 7D show that Msx1 interacts with mTOR kinase domain and inhibits mTOR signaling.

In FIG. 7A, Msx1 interacts with mTOR. HEK 293 cells were transfected with Flag-vector or Flag-Msx1 and then whole cell lysate was immunoprecipitated with mTOR followed by immunoblotting with anti-Flag antibody for Msx1 and anti-mTOR antibody. Expression of Msx1 was confirmed by immunoblotting with anti-Msx1 antibody.

Figure 7B:
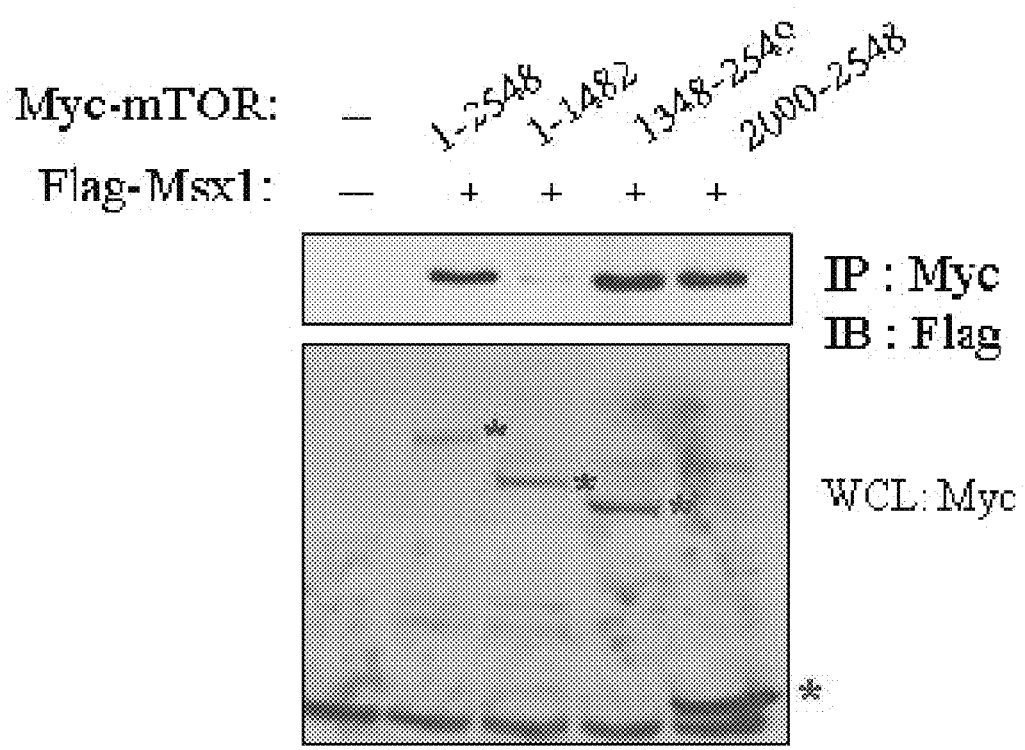

In FIG. 7B, Msx1 interacts with kinase domain of mTOR. To further map Msx1-interacting mTOR domain, HEK 293 cells were transfected with control myc-vector or indicated myc-mTOR expression construct (mTOR domain structure is shown) then whole cell lysates were immunoprecipitated with anti-myc beads followed by immunoblotting with anti-Flag antibody. Transfected whole cell lysates were also used to check expression of indicated mTOR domain by immunoblot analysis with anti-myc antibody.

Figure 7C:
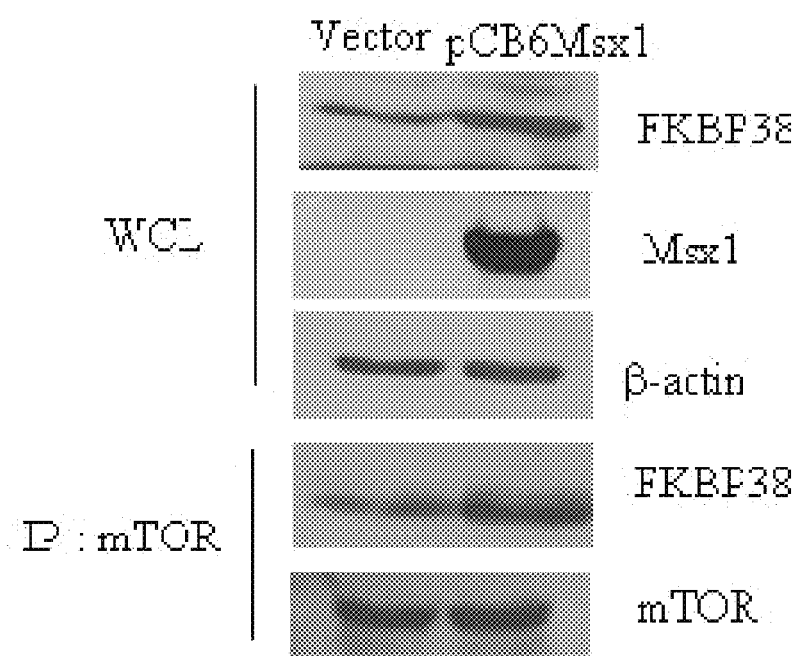

In FIG. 7C, Msx1 enhanced mTOR-FKBP38 interaction. HEK 293 cells were transfected with control vector or pCB6 Msx1 expression construct and then whole cell lysates containing equal amounts of β-actin were immunoprecipitated with anti-mTOR antibody followed by immunoblotting with anti-FKBP38 antibody. Transfected whole cell lysates were also used to check expression of Msx1 and FKBP38 by immunoblot analysis with anti-Msx11 and anti-FKBP38 antibody, respectively.

Figure 7D:
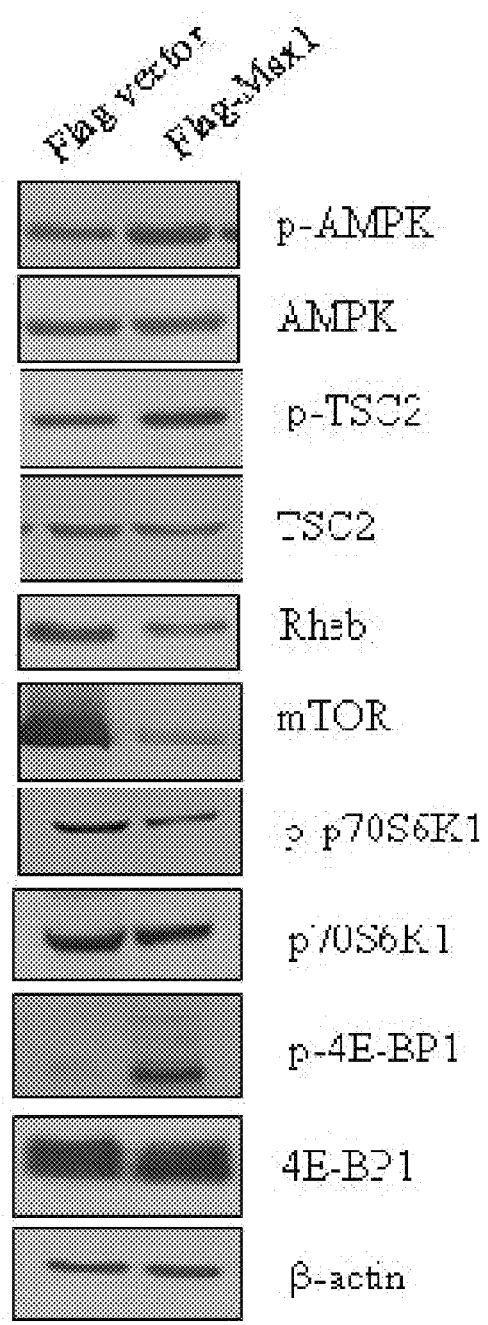

In FIG. 7D, Msx1 suppresses mTOR signaling. HEK 293 cells were transfected with Flag-control vector or Flag-Msx1 expression construct and then whole cell lysates containing equal amounts of β-actin were immunoblotted with indicated antibody to the known mTOR upstream and downstream signaling.

REFERENCES

Abate-Shen, C. (2002). Deregulated homeobox gene expression in cancer: cause or consequence Nature reviews 2, 777-785.

Cone, R. D., and Mulligan, R. C. (1984). High-efficiency gene transfer into mammalian cells: generation of helper-free recombinant retrovirus with broad mammalian host range. Proceedings of the National Academy of Sciences of the United States of America 81, 6349-6353.

Folkman, J. (1986). How is blood vessel growth regulated in normal and neoplastic tissue? G. H. A. Clowes memorial Award lecture. Cancer research 46, 467-473.

Folkman, J. (1989). Successful treatment of an angiogenic disease. The New England journal of medicine 320, 1211-1212.

Folkman, J. (1995). Angiogenesis in cancer, vascular, rheumatoid and other disease. Nature medicine 1, 27-31.

Folkman, J. (2007). Angiogenesis: an organizing principle for drug discovery? Nat Rev Drug Discov 6, 273-286.

Gastl, G., Hermann, T., Steurer, M., Zmija, J., Gunsilius, E., Unger, C., and Kraft, A. (1997). Angiogenesis as a target for tumor treatment. Oncology 54, 177-184.

Guba, M., von Breitenbuch, P., Steinbauer, M., Koehl, G., Flegel, S., Hornung, M., Bruns, C. J., Zuelke, C., Farkas, S., Anthuber, M., et al. (2002). Rapamycin inhibits primary and metastatic tumor growth by antiangiogenesis: involvement of vascular endothelial growth factor. Nature medicine 8, 128-135.

Hanahan, D., and Folkman, J. (1996). Patterns and emerging mechanisms of the angiogenic switch during tumorigenesis. Cell 86, 353-364.

Hartford and Rataini, M. J. (2007). Rapanycin: something old, something new, sometimes borrowed and now renewed. Clinical Pharmacology and Therapeutics. 82, 381-388.

Hwang, E. S., Kim, J., Kim, J. S., Kao, C., Ko, S. C., Chung, L., and Lee, J. H. (1998). The effects of the adenovirus-mediated wild-type p53 delivery in human epithelial ovarian cancer cell line in vitro and in vivo. Int J Gynecol Cancer 8, 27-36.

Karavanas, G., Marin, M., Salmons, B., Gunzburg, W. H., and Piechaczyk, M. (1998). Cell targeting by murine retroviral vectors. Critical reviews in oncology/hematology 28, 7-30.

Landen, C. N., Jr., Birrer, M. J., and Sood, A. K. (2008). Early events in the pathogenesis of epithelial ovarian cancer. J Clin Oncol 26, 995-1005.

Lee, S. H., Son, M. J., Oh, S. H., Rho, S. B., Park, K., Kim, Y. J., Park, M. S., and Lee, J. H. (2005). Thymosin {beta}(10) inhibits angiogenesis and tumor growth by interfering with Ras function. Cancer research 65, 137-148.

Lee, S. H., Zhang, W., Choi, J. J., Cho, Y. S., Oh, S. H., Kim, J. W., Hu, L., Xu, J., Liu, J., and Lee, J. H. (2001). Overexpression of the thymosin beta-10 gene in human ovarian cancer cells disrupts F-actin stress fiber and leads to apoptosis. Oncogene 20, 6700-6706.

Logan, J., and Shenk, T. (1984). Adenovirus tripartite leader sequence enhances translation of mRNAs late after infection. Proceedings of the National Academy of Sciences of the United States of America 81, 3655-3659.

Mackett, M., Smith, G. L., and Moss, B. (1982). Vaccinia virus: a selectable eukaryotic cloning and expression vector. Proceedings of the National Academy of Sciences of the United States of America 79, 7415-7419.

Naora, H. (2005). Developmental patterning in the wrong context: the paradox of epithelial ovarian cancers. Cell cycle (Georgetown, Tex. 4, 1033-1035.

Olsson, A. K., Dimberg, A., Kreuger, J., and Claesson-Welsh, L. (2006). VEGF receptor signalling—in control of vascular function. Nat Rev Mol Cell Biol 7, 359-371.

Park, K., Kim, K., Rho, S. B., Choi, K., Kim, D., Oh, S. H., Park, J., Lee, S. H., and Lee, J. H. (2005). Homeobox Msx1 interacts with p53 tumor suppressor and inhibits tumor growth by inducing apoptosis. Cancer research 65, 749-757.

Uhr, J. W., Scheuermann, R. H., Street, N. E., and Vitetta, E. S. (1997). Cancer dormancy: opportunities for new therapeutic approaches. Nature medicine 3, 505-509.

Weidner, N., Semple, J. P., Welch, W. R., and Folkman, J. (1991). Tumor angiogenesis and metastasis—correlation in invasive breast carcinoma. The New England journal of medicine 324, 1-8.

Zhang, H., Hu, G., Wang, H., Sciavolino, P., Iler, N., Shen, M. M., and Abate-Shen, C. (1997). Heterodimerization of Msx and Dlx homeoproteins results in functional antagonism. Molecular and cellular biology 17, 2920-2932.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method of inhibiting angiogenesis of vascular endothelial cell in a subject with a tumor, the method comprising
selecting a subject with tumor vascular endothelial cells having upregulation of the mTOR pathway; and
administering to said subject a therapeutically effective amount of Msx1 protein comprising the amino acid sequence of SEQ ID NO:1,
wherein inhibition of angiogenesis is achieved by direct interaction of the Msx1 protein with mTOR resulting in downregulation of mTOR.

2. The method of claim 1, wherein the administering comprises expressing in the subject the Msx 1 protein.

3. The method of claim 2, wherein the administering comprises introducing an adenoviral vector or plasmid including a nucleotide sequence encoding the Msx1 protein and expressing the Msx 1 protein in the subject.

4. The method of claim 1, wherein the tumor is selected from the group consisting of ovarian cancer, colon cancer, cervical cancer, lung cancer, lymphoma, breast cancer, prostate cancer, and renal cell cancer.

5. A method of inhibiting tube formation of vascular endothelial cells of a tumor, the method comprising
identifying tumor vascular endothelial cells having upregulation of the mTOR pathway; and
administering to the tumor vascular endothelial cells an amount of Msx1 protein comprising SEQ ID NO:1 effective for inhibiting tube formation,
wherein inhibiting tube formation is achieved by direct interaction of the Msx1 protein with mTOR resulting in downregulation of mTOR.

6. The method of claim 5, wherein the Msx1 protein inhibits vessel sprouting ex vivo.

7. The method of claim 5, wherein the Msx1 protein inhibits vessel formation in vivo.

8. A method of inhibiting angiogenesis in a subject with an angiogenesis-associated disease comprising
selecting a subject having an upregulation of the mTOR pathway in the vascular endothelial cells of angiogenesis-associated disease tissue; and
administering to said subject a therapeutically effective amount of Msx1 protein comprising the amino acid sequence of SEQ ID NO:1,
wherein inhibition of angiogenesis is achieved by direct interaction of the Msx1 protein with mTOR resulting in downregulation of mTOR.

\* \* \* \* \*